US011543404B2

(12) United States Patent
Aiba et al.

(10) Patent No.: US 11,543,404 B2
(45) Date of Patent: Jan. 3, 2023

(54) NERVE CELL DEVICE AND METHOD FOR EVALUATING NEURAL ACTIVITY

(71) Applicant: Stem Cell & Device Laboratory, Inc., Kyoto (JP)

(72) Inventors: Kazuhiro Aiba, Kyoto (JP); Norie Tooi, Kyoto (JP); Kosuke Hori, Kyoto (JP); Masaki Sudo, Kyoto (JP)

(73) Assignee: STEM CELL & DEVICE LABORATORY, INC., Kyoto (JP)

( * ) Notice: Subject to any disclaimer, the term of this patent is extended or adjusted under 35 U.S.C. 154(b) by 2 days.

(21) Appl. No.: 16/763,944

(22) PCT Filed: Nov. 15, 2018

(86) PCT No.: PCT/JP2018/042207
§ 371 (c)(1),
(2) Date: May 13, 2020

(87) PCT Pub. No.: WO2019/098256
PCT Pub. Date: May 23, 2019

(65) Prior Publication Data
US 2021/0025870 A1     Jan. 28, 2021

(30) Foreign Application Priority Data

Nov. 16, 2017   (JP)  .............................. JP2017-220526
Jun. 20, 2018   (JP)  .............................. JP2018-116818

(51) Int. Cl.
*G01N 33/50*     (2006.01)
*C12N 11/082*     (2020.01)
*C12N 11/089*     (2020.01)
*C12N 5/0793*     (2010.01)
*C12N 11/096*     (2020.01)

(52) U.S. Cl.
CPC ....... *G01N 33/5058* (2013.01); *C12N 5/0619* (2013.01); *C12N 11/082* (2020.01); *C12N 11/089* (2020.01); *C12N 11/096* (2020.01); *C12N 2533/30* (2013.01)

(58) Field of Classification Search
CPC .......................... G01N 33/5058; C12N 11/082; C12N 11/096; C12N 11/089; C12N 5/0619; C12N 2533/30
USPC .......................................................... 435/29
See application file for complete search history.

(56) References Cited

U.S. PATENT DOCUMENTS

| 2007/0269481 A1 | 11/2007 | Li | |
| 2008/0207900 A1* | 8/2008 | Kimura | A61P 3/00 544/74 |
| 2016/0116459 A1 | 4/2016 | Managan et al. | |

FOREIGN PATENT DOCUMENTS

| JP | 5249785 B2 | 4/2013 |
| JP | 2017-528127 A | 9/2017 |

OTHER PUBLICATIONS

Amazon, BD 353075 Falcon Clear Polystyrene 96 Well Cell Culture Plate, Accessed Nov. 17, 2020, Available online at: www.amazon.com/BD-353075-Polystyrene-Culture-Low-Evaporation/dp/B0090SES4M.*
Mammadov et al., Neural differentiation on synthetic scaffold materials, Biomaterials Science, vol. 1, (2013), pp. 1119-1137.*
International Search Report and Written Opinion, PCT/JP2018/042207, dated Apr. 9, 2019.
Dermutz et al., "Paper-based patterned 3D neural cultures as a tool to study network activity on multielectrode arrays", RSC Advances, Aug. 11, 2017, vol. 7, pp. 39359-39371.
Lee et al., "Fabrication of a Highly Aligned Neural Scaffold via a Table Top Stereolithography 3D Printing and Electrospinning", Tissue Engineering Part A, New Rochelle, vol. 23, Iss. 11-12, Jan. 11, 2017, pp. 491-502.

* cited by examiner

*Primary Examiner* — Jennifer M. H. Tichy
(74) *Attorney, Agent, or Firm* — Gavrilovich, Dodd & Lindsey LLP (57) ABSTRACT

The present invention provides a nerve cell device in which early observation of nerve activity (spikes, bursts, and the like) is made possible and the measured electric strength is increased by cultivating neurons upon a cell scaffold. By using this nerve cell device, imaging of intracellular signaling is also possible.

10 Claims, 7 Drawing Sheets

NERVE CELL DEVICE AND METHOD FOR EVALUATING NEURAL ACTIVITY

CROSS REFERENCE TO RELATED APPLICATIONS

This application is a U.S. National Phase Application filed under 35 U.S.C. § 371 and claims priority to International Application No. PCT/JP2018/042207, filed Nov. 15, 2018, which application claims priority under 35 U.S.C. § 119 to Japanese Application No. 2017-220526, filed Nov. 16, 2017 and Japanese Application No. 2018-116818, filed Jun. 20, 2018, the disclosures of which are incorporated herein by reference.

TECHNICAL FIELD

The present invention relates to a novel nerve cell device for measuring neural activity.

BACKGROUND ART

In evaluation of safety in drug development, neurotoxicity, as well as cardiac toxicity and hepatotoxicity, is one of main causes by which drug development is discontinued. Therefore, it is necessary to evaluate accurately the neurotoxicity from the initial stage of the development of the medicine, but the evaluation of neurotoxicity in non-clinical studies is mainly based on an in vivo evaluation system such as symptom observation by animal experiments and evaluation of the pathological tissue of the brain, and no convenient in vitro evaluation system for assessing neurotoxicity has not been established. Neural activity is based on the electric activity expressed by the interaction of a plurality of neurons. In recent years, as an in vitro test system, a method for observing the activity of neurons has been developed, in which neurons derived from isolated neurons or pluripotent stem cells are dispersed onto and cultured on a multi-electrode array (hereinafter abbreviated as MEA) to reconstruct a neural network, so as to observe the neural activity by measuring extracellular field potential (non-patent documents 1), and the studies evaluating neurotoxicity using the method have been reported (non-patent documents 2 and 3). As well, to observe neural activity, measurement and visualization of intracellular signals such as membrane potential and intracellular calcium are performed. It has been reported that the changes in membrane potential or changes in intracellular calcium concentration can be measured with a voltage-sensitive dye or a calcium-sensitive dye incorporated into the cells; and that such changes can be measured with a voltage-sensitive fluorescent protein or a calcium-sensitive fluorescent protein expressed in neurons (non-patent documents 4-6).

While the culturing neurons is generally thought to be difficult, the various means providing a scaffold for the neurons to adhere to promote proliferation of neurons have been reported. For example, it has been reported that the proliferation of neurons is promoted by seeding neurons on a scaffold in which microfibers composed of polycaprolactone or polycaprolactone mixed with gelatin are aligned and embedded in a porous three-dimensional hydrogel (non-patent document 7). There are several reports relating to scaffold materials used as a cell scaffold for the purpose of application to medical materials and the like. For example, it has been reported that a cell culture or tissue regeneration is effectively performed by using a cell scaffold material composed of a nano-fiber, for example, polyolefin, polyamide, polyurethane, polyester, fluorine-based polymer, polylactic acid, polyvinyl alcohol, or the like, or the nano-fiber obtained by adsorbing a protein component (patent document 1); by using a three-dimensional cell culture using a cell scaffold material having a hollow fiber membrane mesh and a nano-fiber layer, nutrients and oxygen are supplied to the cultured cells and metabolite wastes are removed from the cultured cells at high efficiency (patent document 2); by using a cell scaffold material composed of a nano-fiber containing gelatin, collagen or cellulose or the nano-fiber which is cross-linked, a large amount of pluripotent stem cells are supplied and cell death is suppressed (patent document 3); by using a cell scaffold material in which polyglycolic acid is used as a support and a nanofiber composed of polyglycolic acid, gelatin or the like is applied thereon, the growth rate of human pluripotent stem cells is improved (patent document 4). However, in the measurement of extracellular field potential by the MEA, there have been no reports of a means for detecting an electric signal at an early stage after the start of culturing neurons or a means for obtaining an enhanced electric signal. Further, there have been no report of a means for detecting changes in intracellular signal at an early stage after the start of culturing neurons.

PRECEDENT TECHNICAL LITERATURE

Patent Document

Patent Document 1: JP-A-2006-254722
Patent Document 2: JP-A-2011-239756
Patent Document 3: JP-A-2013-247943
Patent Document 4: WO 2016/068266

Non-Patent Document

Non-patent Document 1: Odawara, A., et al. Scientific Reports 2016 May 18; 6: 26181.
Non-patent Document 2: Kraushaar, U., et al. Stem Cell-Derived Models in Toxicology, Methods in Pharmacology and Toxicology, 293-308, Mike Clements and Liz Roquemore (eds.), Springer Science New York 2017.
Non-patent Document 3: Schmidt, B. Z., et al. Arch Toxicol (2017) 91: 1-33.
Non-patent Document 4: Grienberger, C and Konnerth, A., Neuron 73, 862-885, 2012.
Non-patent Document 5: Antic, S. D., et al. J Neurophysiol. 116: 135-152, 2016.
Non-patent Document 6: Miller, E. W., Curr Opin Chem Biol. 33: 74-80, 2016.
Non-patent Document 7: Lee, S. J., et al. Tissue Eng Part A. 2017 June; 23 (11-12): 491-502.

SUMMARY OF INVENTION

Issues Invention is to Address

There are various problems in evaluating neural activity using an MEA. For example, neurons seeded directly onto a measurement probe require a long-term culture of 5-6 weeks or more until they can be used for measurement of neural activity. Conventional direct seeding to probes or the like tends to cause instability in the evaluation of neural activity, such as loss of uniformity in terms of cell maintenance due to detachment or aggregation of the cells; In the case of long-term cell culture, it is more likely that undesirable events (detachment or aggregation of cells, contamination, etc.) will occur during the cell culture, and if such events occur, the cost and time spent on the cell culture up to that point will be wasted; and for long-term cell culture, a high maintenance cost is required; and in the current cell culture mode, it is impossible to supply the cell in a readily usable state for neural activity observation. Problems associated with long-term culture of neurons are also caused in evaluating neural activity by intracellular signal imaging method.

The purpose of the present invention is to overcome the problems of the conventional technique.

Means for Addressing the Issues

The present inventors have found that a nerve cell device for culturing neurons on a cell scaffold can be provided as a result of intensive studies in order to overcome the problem of the conventional technique, and the present invention has been completed.

That is, the purpose of the present invention is achieved by the following invention.
(1) A nerve cell device comprising a cell scaffold and neurons.
(2) The nerve cell device according to (1), wherein the neurons are oriented.
(3) The nerve cell device according to (1), wherein the cell scaffold is a fiber sheet formed of a polymeric material.
(4) The nerve cell device according to (3), wherein the fiber sheet has an oriented structure, a non-oriented structure or a mixed structure of orientation and non-orientation.
(5) The nerve cell device according to (3), wherein the fiber sheet is coated with the extracellular matrix protein selected from polylysine, polyornithine, laminin, fibronectin, MATRIGEL (registered trademark) and GELTREX (registered trademark).
(6) The nerve cell device according to any one of (1) to (5), wherein the neurons form a three-dimensional structure on the cell scaffold and/or in the cell scaffold.
(7) The nerve cell device according to any one of (1) to (6), wherein the neurons are neural cells derived from primary cultured cells or pluripotent stem cells.
(8) The nerve cell device according to (7), wherein the neural cells derived from the primary cultured cells or pluripotent stem cells are neural cells derived from mammals.
(9) The nerve cell device according to any one of (1) to (8), wherein the neurons comprise glutamatergic, dopaminergic, gamma-aminobutyratergic, monoaminergic, histaminergic or cholinergic neurons.
(10) The nerve cell device according to any one of (1) to (9), wherein the neurons are seeded at a density of $1 \times 10^4$ cells/cm$^2$ to $4 \times 10^6$ cells/cm$^2$ against the cell scaffold.
(11) The nerve cell device according to any one of (1) to (10), further comprising a frame for holding the periphery of the nerve cell device.
(12) The nerve cell device according to (11), wherein the frame has a longitudinal length×a lateral length of 2 mm×2 mm to 15 mm×15 mm respectively; and the frame is circular or polygonal.
(13) A method for evaluating neural activity using the nerve cell device according to any one of (1) to (12).
(14) A method for evaluating neural activity, comprising contacting the nerve cell device according to any one of (1) to (12) with a multi-electrode array; and measuring extracellular field potential of neural cells included in the nerve cell device.
(15) A method for evaluating neural activity using intracellular signal imaging substance, comprising using the nerve cell device according to any one of (1) to (12).
(16) The method according to (15), wherein the intracellular signal imaging substance is a fluorescent calcium indicator or a fluorescent voltage indicator.
(17) A nerve cell device mounting dish comprising the nerve cell device according to any one of (1) to (12).
(18) A nerve cell device mounting plate comprising the nerve cell device according to any one of (1) to (12) included in at least one of the wells in a multi-well plate having a plurality of wells.

Advantageous Effects of Invention

According to the present invention, by culturing neurons using a cell scaffold, cell adhesiveness is improved, and stable culture including reduction of detachment of the cells during culture or the like has become possible. As a result, by using the nerve cell device of the present invention, a period until a neural activity such as spikes, bursts, or the like is to be measured can be shortened without causing the detachment of seeded neurons from an electrode of a multi-electrode array. Furthermore, since aggregation of neurons is suppressed, high-frequency spikes can be observed. In the nerve cell device of the present invention, intracellular signal imaging has also become possible. The nerve cell device is useful for neurotoxicity evaluation and drug screening for neurological diseases.

BRIEF DESCRIPTION OF THE DRAWINGS

FIG. 1A-D This figure depicts the optical micrographs (magnification×4) showing the state of a cell sheet obtained by seeding iPS cell-derived neurons on an oriented fiber sheet (a) or a random fiber sheet (b) and culturing them for 6 days. (c) is an immunostaining image (magnification×4) of neurons seeded on an oriented fiber sheet using an anti-MAP2 antibody. (d) shows the number of spikes and bursts of neurons seeded on an oriented fiber sheet or on a random fiber sheet.

FIG. 2A-B This figure depicts the optical micrographs (magnification×4) showing the state of a cell sheet obtained by seeding iPS cell-derived neurons on a culture dish (a) or an electrode (b) culturing them for 1-2 days.

FIG. 3A-F This figure depicts the optical micrographs (magnification×4) showing a state of a cell sheet obtained by seeding neurons derived from 253G1 iPS cell-derived neuron and XCL-1 NEURONS on a cell scaffold, and culturing them for 1-3 weeks, using Medium A, B, and C for 253G1 iPS cell-derived neurons and XCL-1 NEURONS, respectively. FIGS. 3a, 3b and 3c: aligned PLGA fibers were used as a cell scaffold. FIGS. 3d, 3e and 3f: As a cell scaffold, a probe (electrode) coated with 0.003% poly-L-lysine and 20 µg/ml laminin was used.

FIG. 4A-D This figure depicts the effect of a cell scaffold on extracellular field potential of iPS cell-derived neuron XCL-1 NEURONS measured using an MEA probe. NFD: Cells were seeded on an aligned PLGA fiber sheet. probe: Cells were seeded directly on an MEA probe. FIG. 4b shows the potential measured after two weeks of culturing under high density seeding conditions. FIG. 4c shows the number of spikes measured after 4 weeks of culturing under low density or high density seeding conditions. FIG. 4d shows the number of spikes measured after 6 weeks of culturing under low density or high density seeding conditions.

FIG. 6A-B This figure depicts an optical micrograph and the result of measurement of neural activity using an MEA probe of a cell sheet obtained by culturing iPS cell-derived neurons iCell GlutaNeurons on an aligned polystyrene fiber sheet. FIG. 6b: Neural activity (spikes and synchronous bursts) was measured using an MEA probe with a cell sheet obtained by seeding with $12 \times 10^5$ cells/cm² and culturing them for two weeks.

FIG. 7A-B This figure depicts the effect of a cell scaffold on drug (4-aminopyridine) response of neurons. NFD: Cells were seeded on an oriented PLGA fiber sheet. probe: Cells were directly seeded on an MEA probe. FIG. 7b: The number of bursts was measured after 6 weeks of culturing iPS cell-derived neuron XCL-1 NEURONS.

FIG. 8A-C This figure depicts the drug (4-aminopyridine) response of iPS cell-derived neuron XCL-1 NEURONS seeded at a high density ($24 \times 10^5$ cells/cm²) on an aligned PLGA fiber sheet. FIG. 8b: It shows a result of analyzing the number of synchronous bursts on a cell sheet obtained after 4 weeks of culturing. FIG. 8c: The result of analyzing the number of spikes and the number of synchronous bursts of a cell sheet obtained after 6 weeks of culturing is shown by raster plot.

MODES FOR EMBODYING TECHNOLOGY IN DISCLOSURE

The cell scaffold used in a nerve cell device of this invention is composed of a fiber produced from a polymeric material. The cell scaffold is preferably a fiber sheet comprising a shape of a sheet in which fibers are integrated. The fiber sheet can have an orientated structure, a non-oriented structure, or a mixed structure of orientation and non-orientation. The oriented structure is a structure in which fibers constituting a fiber sheet are aligned in one direction, and when the angle in one direction is set to 0°, 80% or more of fibers are present in a range of ±30°. In the oriented structure, the distance between the fibers is not particularly limited, but is preferably 5 to 50 µm. The non-oriented structure is a structure in which the directions of fibers are randomly arranged. The polymeric material constituting the fiber is preferably a biodegradable or non-biodegradable polymeric material, and examples thereof include, but are not limited to, PLGA (polylactic acid polyglycolic acid), polystyrene (PS), polysulfone (PSU), and polytetrafluoroethylene (PTFE). The diameter of the cross section of the fiber constituting the fiber sheet is not particularly limited, but is, for example, 0.1 to 8 µm, preferably 0.5 to 7 µm, and more preferably 1 to 6 µm. The thickness of the fiber sheet is, for example, 1 to 40 µm, preferably 5 to 35 µm, and more preferably 10 to 30 µm. The opening ratio of the fibers constituting the fiber sheet can vary depending on the polymeric material used. The opening ratio is not particularly limited, but is, for example, 10 to 50%, preferably 15 to 45%, and more preferably 20 to 40%. Here, the opening ratio refers to a ratio of an area in which no fiber exists with respect to a fixed area of a fiber sheet plane.

The fiber sheet can be produced, for example, by using an electrospinning method from a solution containing a polymeric material. In the case of manufacturing a fiber sheet having an oriented structure, a fiber sheet can be produced by, for example, using a rotary drum, spraying a solution containing a polymer material to a rotary surface of the drum from a nozzle while rotating the drum, and winding the fiber formed on the rotary drum. In the case of manufacturing a fiber sheet having a non-oriented structure, a fiber sheet can be produced by spraying a solution containing a polymeric material onto a flat plate. In the case of manufacturing a fiber sheet having a mixed structure of an oriented structure and a non-oriented structure, for example, the fiber sheet having an oriented structure and a non-oriented structure can be produced by combining the above production methods.

As a polytetrafluoroethylene (PTFE) sheet, for example, a commercially available pore chlorofluorocarbon (registered trademark) of Sumitomo Electric Industries, Ltd. can be used.

As a solution of the polymeric material, an organic solvent in which the polymer material to be used is dissolved at 10 to 30 wt. % at room temperature may be used. For example, 1,1,1,3,3,3-hexafluoro-2-propanol (HFIP), N,N-dimethylformamide (DMF) and the like can be used.

The fiber sheet is fixed or held at periphery with a frame. When the frame is fixed or held on the fiber sheet, there is no particular limitation as long as it does not affect cell culture. For example, a commercially available biocompatible adhesive, for example, a silicone one-liquid condensation type RVT rubber (Shin-Etsu Chemical Co., Ltd., catalog number KE-45) can be used to bond the frame to the fiber sheet.

The material of the frame is not particularly limited as long as it does not affect cell culture. For example, a polydimethylsiloxane (PDMS), PS, polycarbonate, stainless steel or the like is exemplified. The thickness of the frame is not particularly limited, but is 0.1-4 mm, preferably 0.25-3 mm, and more preferably 0.5-2 mm.

The shape of the frame can be changed depending on the purpose of use, and its longitudinal length×its lateral length is preferably 2 mm×2 mm to 15 mm×15 mm, respectively, and is circular or polygonal.

The nerve cell device using the fiber sheet or the fiber sheet by fixing or holding the periphery of the fiber sheet with a frame as a cell scaffold can be arranged as it is in at least one of wells included in a cell culture dish or a multi-well plate having a plurality of wells.

In this specification, a nerve cell means a nerve unit composed of a cell body, dendrites, and axons, and is also referred to as a neuron. The neuron can be classified according to a difference in neurotransmitters produced by the neurons. Examples of the neurotransmitters include: monoamines such as dopamine, noradrenergic, adrenergic and serotonin; non-peptide neurotransmitters such as acetylcholine, gamma-aminobutyric acid and glutamic acid; peptide nerve transfer substance such as adrenal cortex stimulation hormones (ACTH), alpha-endorphins, beta-endorphins, gamma-endorphins, and vasopressin. For example, neurons using dopamine, acetylcholine, and glutamic acid as transfer substances are referred to as dopaminergic neurons, cholinergic neurons, and glutamic acid-activated neurons, respectively.

As the neuron, primary cultured cells can be used. Primary cultured cells are important as a system for evaluating the effect of drugs or the like in a living organism because the primary cultured cells have many intrinsic cell functions in a living organism.

As primary cultured cells, neural cells in central nervous system and peripheral nervous system of a mammalian, for example, rodents as mouse or, rat, or primates as monkey or human can be used. In preparing and culturing these neurons, an animal anatomical method, a tissue collecting method, and a nerve separation/isolation method, the culture medium for culturing neurons, culture conditions and the like can be selected from known methods depending on the type of cells to be cultured and the purpose of cells. As a commercially available primary cultured neural cell product, for example, rat cerebral neurons of Lonza Bioscience and human cerebral neurons of ScienCell Research Laboratories, Inc. can be used.

As neurons, neural cells derived from pluripotent stem cells can be used. Examples of pluripotent stem cells include embryonic stem cells (ES cells) and iPS cells. A variety of types of neural cells can be obtained by differentiating pluripotent stem cells using a known neural differentiation induction method. For example, neural cells can be obtained by a differentiation inducing method using the low-molecular compound described in the literature (Honda et al. Biochemical and biophysical Research Communications 469 (2016) 587-592).

As well, a neural cell product derived from a commercially available pluripotent stem cell, for example, iCell NEURON of Cellular Dynamics International, Inc. and XCL-1 NEURONS of XCell Science Inc. can also be used. These commercially available neural cells are cultured in the medium attached.

The neurons can be co-cultured with astrocytes derived from the brain of mammals. Alternatively, the neuron can be cultured by adding medium after culturing astrocytes (an astrocyte culture supernatant) to the medium for neurons at a final concentration of 5-30%.

In the fiber sheet or the fiber sheet whose periphery is fixed or held by the frame, neural cells suspended in the medium are seeded at a density of $1 \times 10^4$ cells/cm$^2$ to $4 \times 10^6$ cells/cm$^2$, preferably $5 \times 10^4$ cells/cm$^2$ to $3 \times 10^6$ cells/cm$^2$, more preferably $1 \times 10^5$ cells/cm$^2$ to $2 \times 10^6$/cm$^2$ and are cultured for 7 to 14 days while exchanging the medium at 1 to 7 day intervals, therefore the nerve cell device in which the neurons uniformly formed in a three-dimensional structure can be obtained. The formation of a three-dimensional structure means to a state in which neurons adhere along fibers constituting the fiber sheet, penetrate into one side or both sides of the fiber sheet and are glowing.

When neural cells are seeded on a fiber sheet and cultured, the cells are maintained in an uniformly spread state in the culture with little detachment or aggregation of cells which are observed when the neurons are directly seeded on the culture petri dish without using a fiber sheet.

The nerve cell device of the present invention is brought into contact with a multi-electrode array for measuring the extracellular field potential of the neurons included in the nerve cell device under an environment of 5% $CO_2$ and 37° C. The multi-electrode array has multiple planar microelectrodes arranged on a substrate allowing simultaneous observation of electric signals from a plurality of cells.

As a means for measuring neural activity, various intracellular ions and potential changes can be measured in addition to the multi-electrode array. For this purpose, a fluorescent calcium indicator such as a calcium-sensitive dye and a calcium-sensitive fluorescent protein, and a fluorescent potential indicator such as a voltage-sensitive dye and a voltage-sensitive fluorescent protein are used (Grienberger, C and Konnerth, A., Neuron 73, 862-885, 2012; Antic, S. D., et al. J Neurophysiol. 116: 135-152, 2016; Miller, E. W., Curr Opin Chem Biol. 33: 74-80, 2016). Using these indicators, the changes in calcium or field potential obtained with the nerve cell device of the present invention can also be measured by means of a cell imaging device.

Examples of the fluorescent calcium indicator include a calcium-sensitive dye such as Quin-2, Fura-2, Fluo-3, -4 and -8, Indo-1, Rhod-2 and -3, X-Rhod-1, Cal-520, Calbryte (TradeMark), and Ca™. They are usually used as an acetoxymethyl ester for the purpose of imparting permeability to neurons. The acetoxymethyl group is subjected to hydrolysis and is cleaved by intracellular esterase. Further, as the calcium-sensitive fluorescent protein, a gene-code type calcium probe such as Camgaroo-1 and -2, GCaMP-2, -3, -5 and -6, CaMPARI, and Case 12 is known.

Examples of the fluorescent voltage indicator include voltage-sensitive dyes such as Merocyanine 540, Rh1692, Di-4ANEPPS, JPW114, ANNINE-6, Indocyanine Green, Dipicrylamine, FluoVolt (TradeMark). As a potential sensitive fluorescent protein, a gene code type membrane potential probe such as VSFP-1 and -2, FlaSh, SPARC based on green fluorescent protein (GFP) is known (Siegel, M. S. and Isacoff, E. Y. Neuron 19, 735-741, 1997; SaKai, R., Repunte-Canonigo, V., et al. Eur. J Neurosci. 13, 2314-2318, 2001; Ataka, K. and Pieribone, V. A., Biophys J. 82, 509-516, 2002; Akemann, W. Mutoh, H., et al. Nature Methods, 7, 643-649, 2010).

EXAMPLES

Next, the present invention will be described in detail by way of examples, but the present invention is not limited thereto.

Example 1

[Production of Fiber Device]
(1) Production of Random Fiber Sheet

PLGA (SIGMA P1941) or PSU (SIGMA 182443) was dissolved in HFIP (wako 089-04233) at room temperature so as to have a concentration of 20 wt. %, the solution was filled into a syringe (Norm-Ject Syringes 5 ml capacity, Osaka chemical), and the syringe was set to a nano-fiber electric field spinning device NANON-03 (MECC CO., LTD.) and then the fiber sheet was produced on a plate collector under the conditions of, when using PLGA, a needle diameter of 22 G, a voltage of 20 kV and a feeding speed of 1 ml/h, and when using PSU, a needle diameter of 27 G, a voltage of 15 kV and a feeding speed of 1 ml/h.

(2) Production of Oriented Fiber Sheet

PLGA (SIGMA P1941) was dissolved in HFIP (wako 089-04233) at room temperature so as to have a concentration of 20 wt. %, the solution was filled into a syringe (Norm-Ject Syringes 5 ml capacity, Osaka chemical), the syringe was set to a nano-fiber electric field spinning device NANON-03 (MECC CO., LTD.), and then the PLGA fiber sheet was produced on a drum collector under the condition of a needle diameter of 22 G, a voltage of 20 kV, a feeding speed of 1 ml/h, and a rotation speed of 750 rpm. When producing the PSU fiber sheet, PS (Fluka) was dissolved in DMF (N,N-dimethylformamide, wako pure chemical) at room temperature so as to have a concentration of 30 wt. %, the dissolved solution is filled into a syringe (Norm-Ject Syringes 5 ml capacity, Osaka chemical), the syringe was set to a nano-fiber electric field spinning device NANON-03 (MECC CO., LTD.), and then the PSU fiber sheet was produced on a drum collector under conditions of a needle diameter of 25 G, a voltage of 10 kV, a feeding speed of 1.5 ml/h, and a rotation speed of 2,000 rpm.

(3) Frame Adhesion to the Fiber Sheet

A polycarbonate frame (15 mm×15 mm) or a stainless steel circular frame (outer diameter 6 mm, inner diameter 3 mm) was adhered to the prepared fiber sheet by using a silicone one-component condensation type RVT rubber (Shin-Etsu Chemical Co., Ltd., catalog number KE-45) to produce the fiber device.

Example 2

[Preparation of Neurons]
(1) Neural Differentiation Derived from Human iPS Cells (253G1 Line)

Neurons differentiated from human iPS cells 253G1 in accordance with the previous report (Honda et al. Biochemical and Biophysical Research Communications 469 (2016) 587-592) were used. The undifferentiated hiPS cells were seeded on a culture dish coated with poly-L-lysine (PLL, Sigma-Aldrich) and laminin111 (LM, Sigma-Aldrich), and cultured for 7-10 days in a N2B27 nerve medium (medium in which a DMEM/F-12 medium containing a N2 supplement (GIBCO, 17502048) and a Neurobasal medium containing a B27 minus vitamin A supplement is (GIBCO, 12587001) is mixed at 1:1) containing 100 nM LDN193189 (Cellagen Technology) and 1 μM SB431542 (Sigma-Aldrich). Thereafter, the cell colonies were dissociated into small cell clusters by collagenase (GIBCO) and cultured for further 7 to 10 days in a N2B27 nerve medium containing only the LDN1939189, and the resultant cell colonies were again dissociated into cell clumps with collagenase, followed by the continuous culture in a N2B27 medium. In 5-7 days, neurons which become available for the following experiments are obtained. The obtained neurons can be cryopreserved, and the cryopreserved neurons can also be used. In order to cryopreserve neurons, neural aggregates were dissociated into a single cell with Accutase (Innovative Cell Technologies), suspended in a Bambanker (NIPPON genetics Co., Ltd.), frozen at −80° C. and stored in a ultra-low temperature freezer at −150° C. for long-term storage.

(2) Commercial hiPS Cells-Derived Neurons

A commercially available hiPS cell-derived cryopreserved neurons XCL-1 NEURONS (XCell Science Inc., catalog number XN-001-1V) were thawed according to the protocol of XCell science Inc., to obtain a neuron suspension.

Example 3

[Culturing of Human iPS Cell-Derived Neurons]

Figure 1A:
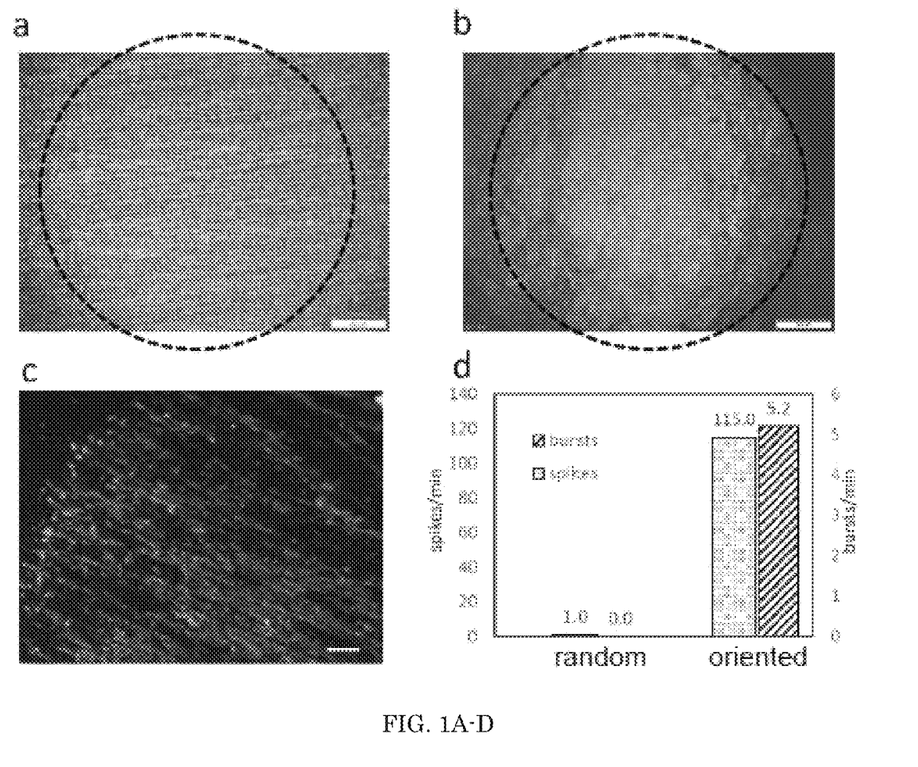
Figure 2A:
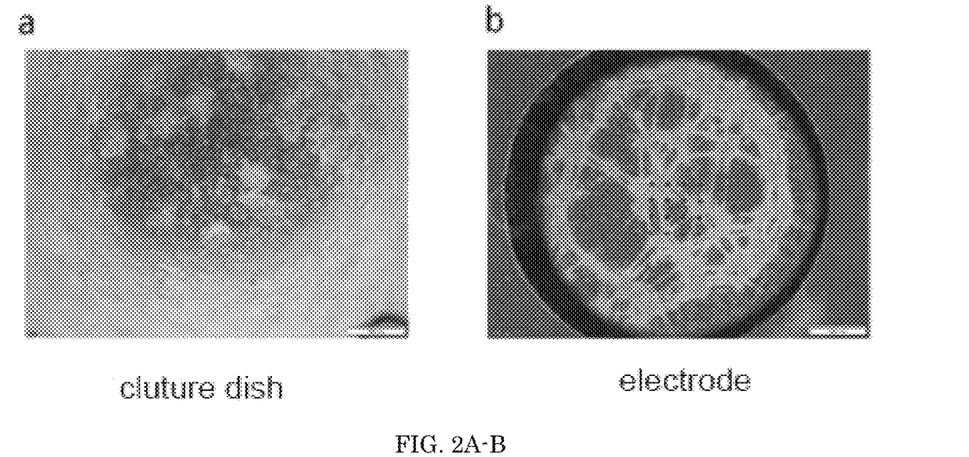

By using the fiber sheet prepared in example 1 as a cell scaffold, iPS cell-derived neurons suspended in a N2B27 medium were seeded on oriented PLGA, random PLGA, random PSU fiber sheet, and PTFE sheet (Sumitomo Electric Industries, Ltd.) at a density of $1.3 \times 10^6$ cells/cm$^2$, and cultured in an incubator at 5% CO$_2$ and 37° C. for 6 days. The results of the obtained cell sheet (nerve cell device) observed by an optical microscope are shown in FIG. 1a (using the oriented PLGA fiber sheet) and FIG. 1b (using the random PSU fiber sheet). As a control, iPS cell-derived neurons were similarly seeded on a culture dish (Nunc (registered trademark) Cell-Culture Treated Multidishes) or an electrode probe commonly used (Alpha MED Scientific Inc./MED probe16/MED-RG515A), and cultured for 1-2 days. The results of the obtained cells observed with an optical microscope are shown in FIG. 2a (on the culture dish) and FIG. 2b (on the electrode). As a result, in the control group, it was shown that no cell sheet was maintained even after 1 day of culture. On the other hand, on the fiber sheet, it was shown that, the cells were growing, spreading out uniformly even after 6 days of culture (FIGS. 1 and 2). After 5 weeks of seeding iPS cell-derived neurons, the cells were fixed with 4% paraformaldehyde (NACALAI TESQUE, INC.) at room temperature for 15 to 30 minutes. After washing with PBS, the cells were treated with 0.2% TritonX-100 (Sigma) at room temperature. After 5 minutes, cells were washed with PBS and blocked with 1% bovine serum albumin for 1 hour at room temperature. Then, the cells were washed with PBS and treated with an anti-MAP2 antibody (Abcam). After 1 hour, the cells were washed with PBS and treated with Alexa Fluor 546-anti-rabbit IgG antibody (Thermo Fisher Scientific K. K.) for one hour. After washing with PBS, it was observed by a fluorescence microscope (KEYENCE CORPORATION) (FIG. 1c). As shown in FIG. 1c, aligned neurons are recognized by staining with a MAP 2 antibody that can stain neuronal axons. FIG. 1d shows the results of MEA measurement detecting the number of spikes and bursts of neurons after 4 weeks from seeding on the random PLGA fiber sheet and the oriented PLGA fiber sheet. It has been found from FIG. 1d that the oriented fiber sheet has an effect in increasing the number of spikes and the number of bursts.

Example 4

[Effect of Type of Culture Medium on Neuronal Adhesion to the Cell Scaffold]

Figure 3A:
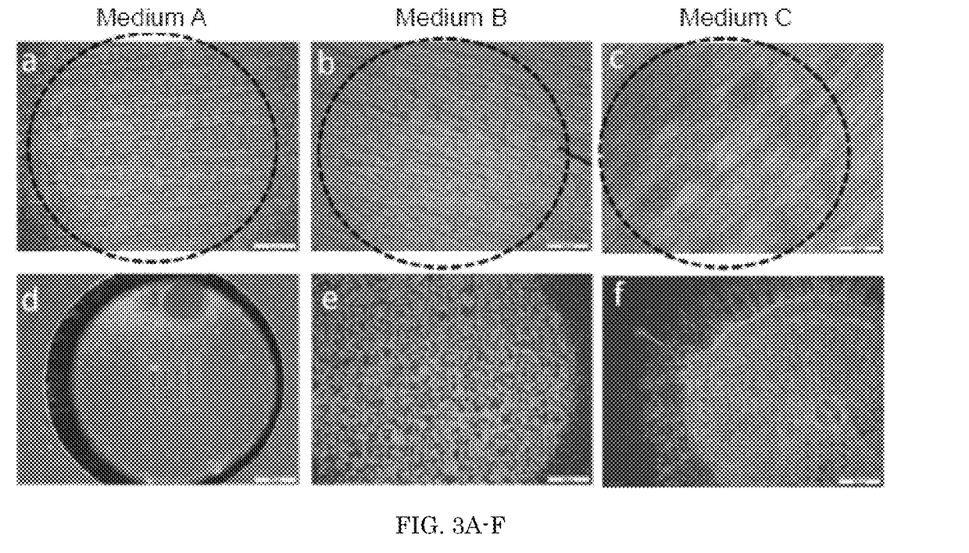

Using 3 different culture media, N2B27 medium containing 20% Astrocyte Conditioned Medium (ACM) (Astrocyte Conditioned Medium-Serum Free (ACM-sf)/11811-sf, ScienCell Research Laboratories Inc.) (Medium A), Neurobasal (registered trademark) medium containing B27 minus vitamin A supplement (Medium B), and BrainPhys (registered trademark) Neuronal Medium (05792, STEMCELL TECHNOLOGIES) containing 20% ACM (Medium C), 253G1 iPS cell-derived neurons and XCL-1 NEURONS (XCell Science, catalog number XN-001-1V) are seeded at a density of $1.2 \times 10^6$ cells/cm$^2$ on a cell scaffold and performed cultural observation. As the cell scaffold, the oriented PLGA fibers coated with 0.002% poly-L-lysine and 20 μg/ml laminin in the case of 253G1 iPS cell-derived neurons and the oriented PLGA fibers coated with 0.002% poly-D-lysine and 10 μg/ml laminin in the case of XCL-1 NEURONS are used. The seeded cells are cultured for 1-3 weeks in an incubator at 5% CO$_2$, 37° C. The results of the obtained cell sheet (nerve cell device) observed by an optical microscope are shown in FIGS. 3a, 3b, and 3c. As a control, neurons were seeded on probes (electrodes) immersed in 10% bovine serum-containing culture medium based on conventional methods, followed by coating with 0.003% poly-L-lysine (Sigma-Aldrich) and 20 μg/ml laminin (Sigma-Aldrich) in the case of the neuron derived from 253G1 iPS cell and, or by coating with 0.02% poly-D-lysine and 10 μg/ml laminin in the case of XCL-1 NEURONS, and then cultured for 1-3 weeks. The results of the obtained cell sheet observed by an optical microscope are shown in FIGS. 3d, 3e and 3f. The seeding density of the cells is $1.3 \times 10^6$ cells/cm$^2$ (FIG. 3d) or $3 \times 10^5$ cells/cm$^2$ (FIGS. 3e and f). As a result in the control group using Medium A, it was observed that neurons detached from the electrodes and the detached neurons formed cell aggregates. Cells formed small colonies in the control groups using Medium B, and detachment of the cells were observed in the periphery of the region where the cells were seeded in the control groups using Medium C. On the other hand, when cells were cultured on the oriented PLGA fiber, the cell sheet was uniformly maintained regardless of the type of the culture media (FIG. 3).

Example 5

Figure 4A:
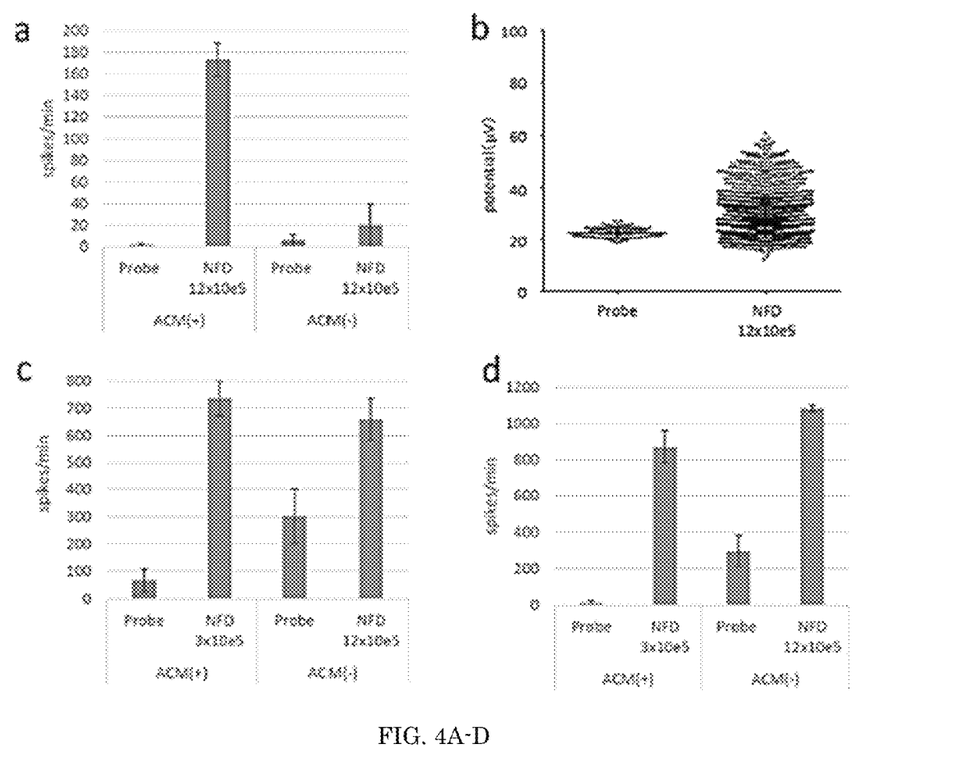
FIG. 4a shows the number of spikes measured after 2 weeks of culturing under high density seeding conditions.

[MEA Measurement of Extracellular Field Potential of Neurons Grown on an Aligned PLGA Fiber Sheet as a Cell Scaffold]

iPS cell-derived neurons XCL-1 NEURONS (XCell Science, catalog number XN-001-1V) were seeded on the oriented PLGA fiber sheet as a cell scaffold at $3 \times 10^5$ cells/cm$^2$ (low-density seeding condition) or $12 \times 10^5$ cells/cm$^2$ (high-density seeding condition), and cultured with BrainPhys (registered trademark) Neuronal Medium (05792, STEMCELL TECHNOLOGIES) with or without 20% ACM in an incubator at 37° C., 5% CO$_2$ for 2, 4 and 6 weeks. The fiber was placed on a multi-electrode array (MEA) probe (MED64 system, Alpha MED Scientific Inc.) to make the cells contact with the electrodes of MEA probe to measure neural activity (spike and burst). In parallel, the neurons were seeded directly on the MEA probe at $3 \times 10^5$ cells/cm$^2$, and cultured in an incubator at 37° C., 5% CO$_2$ for 2, 4 and 6 weeks, and the neural activity was similarly measured. The results are shown in FIG. 4. As a result, compared to a conventional method (the cell seeded on MEA probe), a high frequency spikes were detected in the cells seeded at a high density on an oriented PLGA fiber sheet at an early stage after 2 week-culture (FIG. 4A). This phenomenon was remarkable in neurons on the fiber sheet cultured in medium containing ACM, and an increase in the average potential was also observed (FIG. 4B). Furthermore, in the 4th week after the cell seeding, the spikes and bursts were detected at a higher frequency compared with the conventional method even in neurons on the fiber sheet seeded at a low density (FIG. 4C). In the 6th week neuron, the spikes and bursts were detected at a higher frequency (FIG. 4d).

Figure 5:
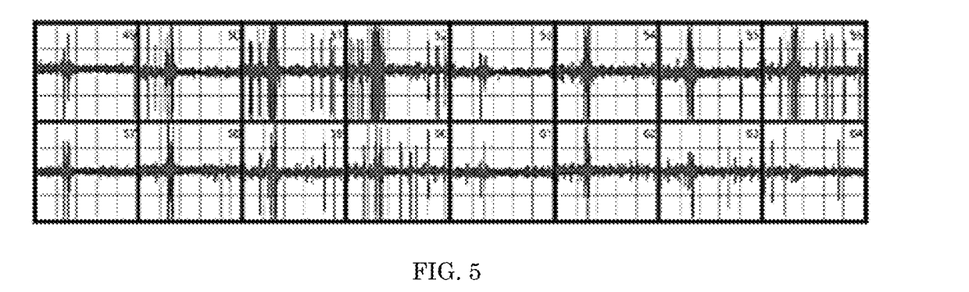

Rat cerebral cortex neurons (Thermo Fisher Scientific K. K., product number A10840), which are primary cultured neurons, were used as neurons, and seeded on the aligned PLGA fiber sheet as a cell scaffold at a cell density of $1.0 \times 10^5$ cells/cm$^2$, $3.0 \times 10^5$ cells/cm$^2$, or $9.0 \times 10^5$ cells/cm$^2$. The cells were cultured with Neurobasal (registered trademark) Medium (GIBCO, catalog number 21103-049) containing 1×B-27 (registered trademark) Supplement/serum-free (GIBCO, catalog number 17504-044) in an incubator at 37° C., 5% CO$_2$ for 1, 2, and 4 weeks. The obtained cell sheet (nerve cell device) was placed on the MEA probe (MED64 system, Alpha MED Scientific Inc.) to make the cells contact with the electrodes of the MEA probe to measure neural activity (spikes and bursts). As a result, spikes and bursts were detected in a nerve cell device cultured 2 and 4 weeks. The results of the MEA measurement detecting extracellular field potential evoked by the cell sheet (nerve cell device) seeded with $9.0 \times 10^5$ cells/cm$^2$ and cultured for 4 weeks are shown in FIG. 5. In each electrode, spikes and synchronous bursts were observed.

Example 6

Figure 6A:
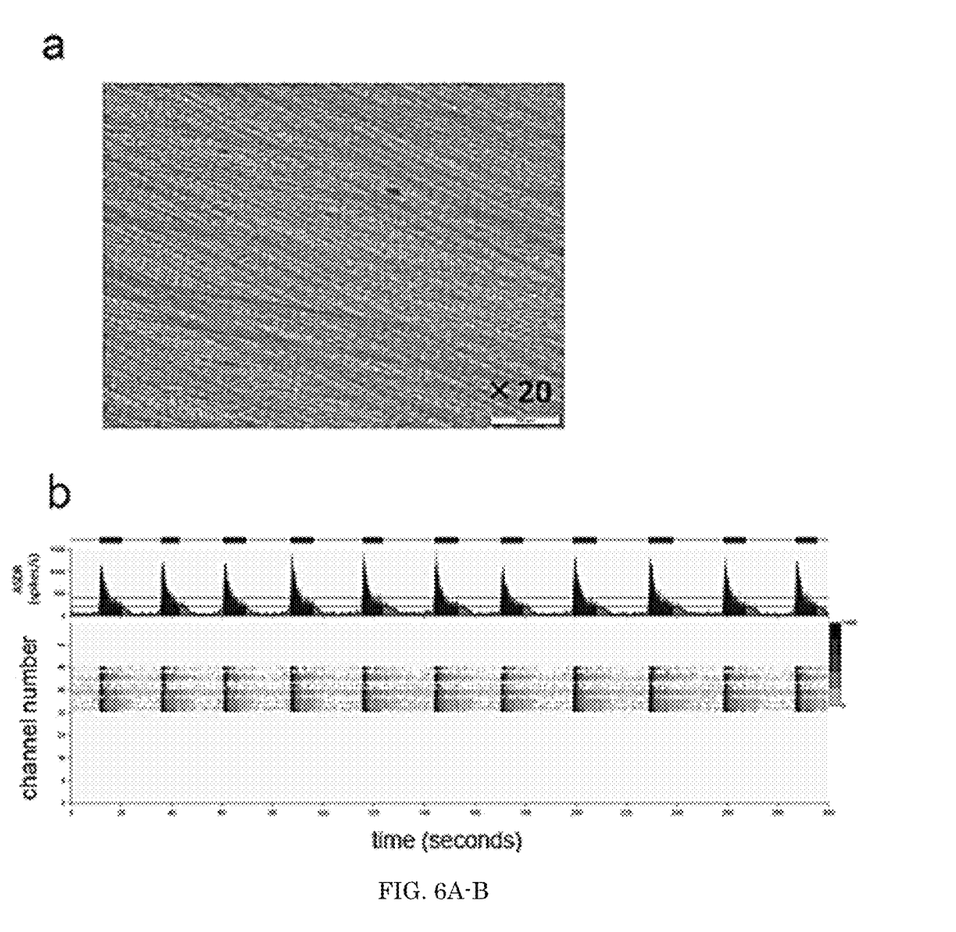
FIG. 6a: It is an optical micrograph (magnification× 20) of a cell sheet obtained by seeding at $12 \times 10^5$ cells/cm² and culturing for 4 weeks.

[MEA Measurement for Extracellular Field Potential of Neurons Grown on an Oriented Polystyrene Fiber Sheet as a Cell Scaffold]

iPS cell-derived neurons iCell (registered trademark) GlutaNeurons (glutamatergic neuron, Cellular Dynamics International Inc., product number GNC-301-030-000.5) were seeded on an oriented polystyrene fiber sheet supported by a circular frame having an outer diameter of 6 mm and an inner diameter of 3 mm as a cell scaffold at a cell density of $8 \times 10^5$ cells/cm$^2$, $12 \times 10^5$ cells/cm$^2$ or $16 \times 10^5$ cells/cm$^2$. These cells were cultured using iCell glutamatergic neuron medium (Cellular Dynamics International Inc.) with or without 20% ACM in an incubator at 5% CO$_2$, 37° C. for 1, 2 and 4 weeks. The photographic images of the cell sheet (nerve cell device) seeded at $12 \times 10^5$ cells/cm$^2$ and cultured with iCell glutamatergic neuron medium without ACM for 4 weeks, which were acquired by an optic microscope, are shown in FIG. 6a. As shown in FIG. 6a, neurons are successfully attached to the polystyrene fiber sheet, and a uniform cell sheet without cell detachment is maintained even when culturing is continued for 4 weeks. Similar results were obtained in the case of a medium containing 20% ACM.

A cell sheet (nerve cell device) seeded with $12 \times 10^5$ cells/cm$^2$ and cultured for 2 weeks in an iCell glutamatergic neuron medium with 20% ACM was placed on an MEA probe (MED64 system, Alpha MED Scientific Inc.), and made the cells contact with the electrodes of the MEA probe to measure neural activity (spikes and synchronous bursts). The detection of the spikes and the synchronous bursts were analyzed by a raster plot using a MED64 Burstscope (Alpha MED Scientific Inc.). The results are shown in FIG. 6b. Even in 2 weeks after culturing, the synchronous bursts were confirmed.

Example 7

Figure 7A:
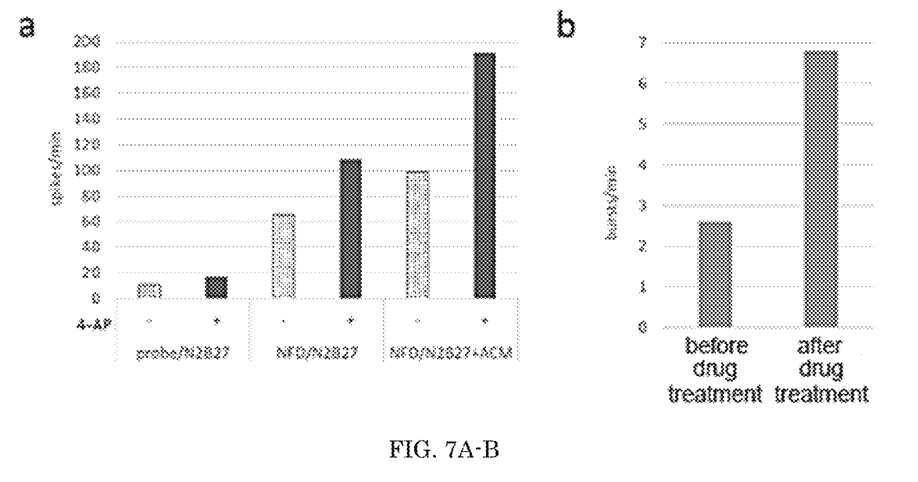
FIG. 7a: The number of spikes was measured after 4 weeks of culturing neurons derived from 253G1 hiPS cells.

[Confirmation of Drug Response of the Neurons Grown on the Aligned PLGA Fiber Sheet as a Cell Scaffold]

iPS cell-derived neurons (253G1 hiPS cell-derived neuron or XCL-1 NEURONS (XCell Science, catalog number XN-001-1V)) were seeded on the oriented PLGA fiber sheet as a cell scaffold at $13 \times 10^5$ cells/cm$^2$. 253G1 hiPS cell-derived neurons were cultured in N2B27 medium with or without 20% ACM, and the XCL-1 NEURONS are cultured in BrainPhys (registered trademark) Neuronal Medium (05792, STEMCELL TECHNOLOGIES) with or without 20% ACM in an incubator at 5% CO$_2$ and 37° C. for 4 or 6 weeks. The fiber sheet was placed on an MEA probe (MED64 system, Alpha MED Scientific Inc.), and made the cells contact with the electrodes of MEA probe to measure neural activity (spikes). As a control, neurons were similarly seeded directly on a probe (electrodes) based on a conventional method, and cultured in an incubator at 5% CO$_2$ and 37° C. for 4 or 6 weeks. The obtained results were compared with those given by a conventional method (direct seeding to a probe). A larger number of spikes were detected in 253G1 hiPS cell-derived neurons on the fiber sheet at 4-week culture (FIG. 7a). Compared to the neurons on the probe, the increase in the number of spikes was 6-fold in the neurons cultured on the fiber sheet of the present invention, and 9-fold in the fiber sheets cultured in the medium with 20% ACM, which means that the number of spikes was significantly increased by using the fiber sheet. In the measurement system, 4-aminopyridine (4-AP), known to have a function of inhibiting various potassium channels in neurons and maintaining neuronal action potential, was added to the neurons cultured for 4 weeks at a final concentration of 100 μM, and then the spikes were measured. As a result, the number of spikes was increased both in the control group and in the fiber sheet group by the addition of 4-aminopyridine, and appropriate drug response was also confirmed (FIG. 7a). The increase in the number of spikes was 167% in the fiber sheet group of the present invention, compared to 156% in the control group cultured on the probe, and 194% in the fiber sheet group cultured in the medium with 20% ACM. XCL-1 NEURONS seeded on the fiber sheet at a density of $12\times10^5$ cells/cm$^2$ and cultured for 6 weeks in the medium with ACM were treated with 4-AP having a final concentration of 100 μM, which resulted in a 2.6-fold increase in the number of bursts (FIG. 7b).

Example 8

[Drug Response of Neurons Seeded at a High Density on the Oriented PLGA Fiber Sheet as a Cell Scaffold]

iPS cell-derived neurons XCL-1 NEURONS (XCell Science, catalog number XN-001-1V)) were seeded on the oriented PLGA fiber sheet as a cell scaffold at $24\times10^5$ cells/cm$^2$, twice as high as in the case of Example 7. The cells were cultured in BrainPhys (registered trademark) Neuronal Medium (05792, STEMCELL TECHNOLOGIES) containing 20% ACM in an incubator at 5% $CO_2$ and 37° C. for 2, 4, and 6 weeks. The obtained cell sheet (nerve cell device) was placed on an MEA probe (MED64 system, Alpha MED Scientific Inc.) and made the cells contact with the electrodes of MEA probe to measure neural activity (spikes and bursts). In the measurement system, 4-aminopyridine (4-AP), known to maintain a neural action potential was added at a final concentration of 100 μM to examine the drug response of neurons. MED 64 Burstscope (Alpha MED Scientific Inc.) was used for analyzing neural activity.

Figure 8A:
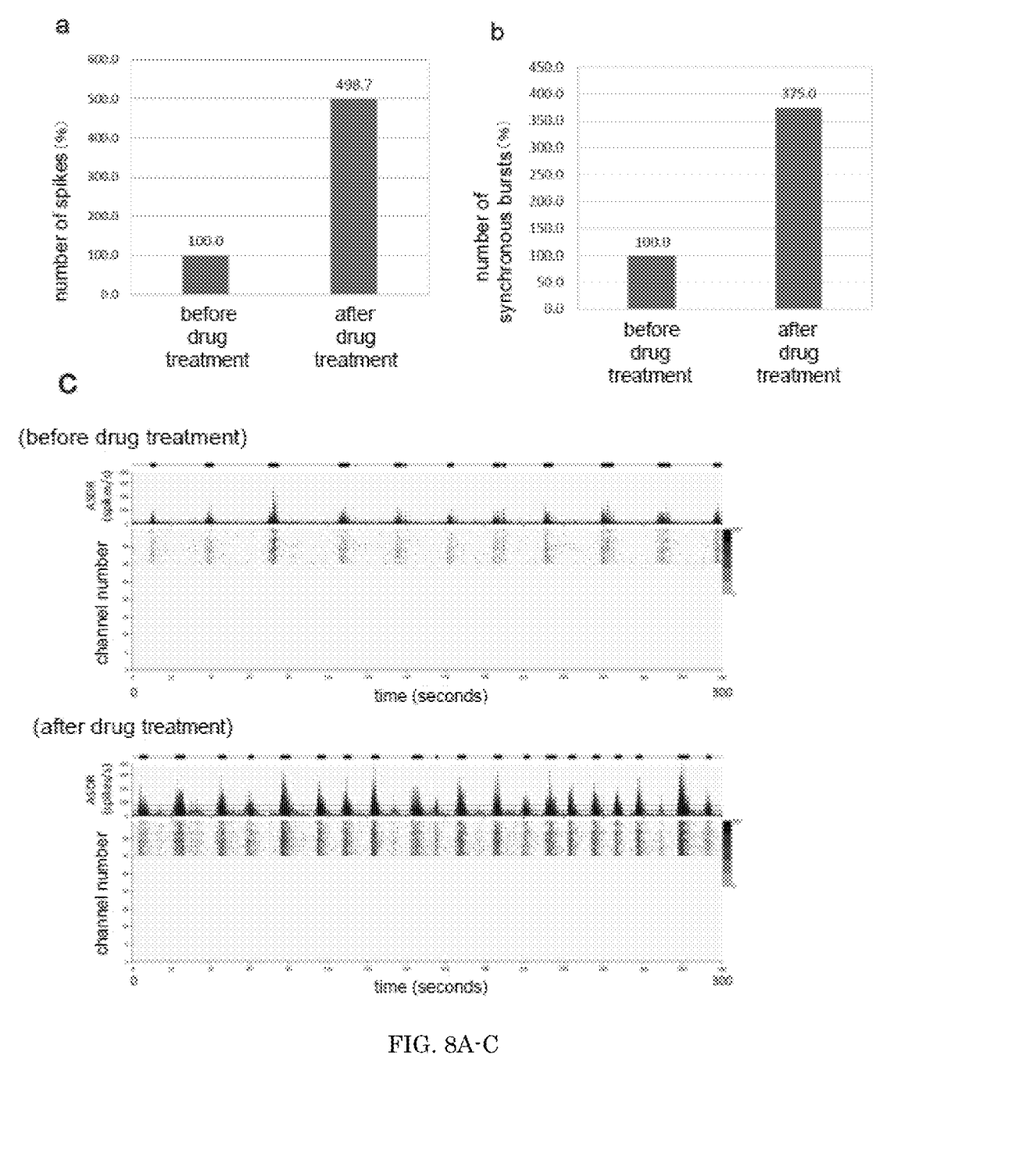
FIG. 8a: It shows the result of analysis of the number of spikes of a cell sheet obtained after 4 weeks of culturing.

About the cell sheet obtained by culturing for 4 weeks, the result of analyzing the number of spikes is shown in FIG. 8a, and the result of analyzing the number of synchronous bursts is shown in FIG. 8b. Treatment with 4-AP resulted in a 499% increase in the number of spikes and a 375% increase in the number of synchronous bursts. Furthermore, the result of analyzing neural activity by raster plots for a cell sheet obtained by culturing for 6 weeks is shown in FIG. 8c. In the raster plots, a remarkable increase in the number of spikes and synchronous bursts due to 4-AP treatment was also observed. These results show that the drug (4-AP) response of neurons is enhanced in the nerve cell device of the present invention.

Example 9

[Observation of Neural Activity by Calcium-Sensitive Dye in Neurons Grown on the Oriented Polystyrene Fiber Sheet as Cell Scaffold]

Figure 9:
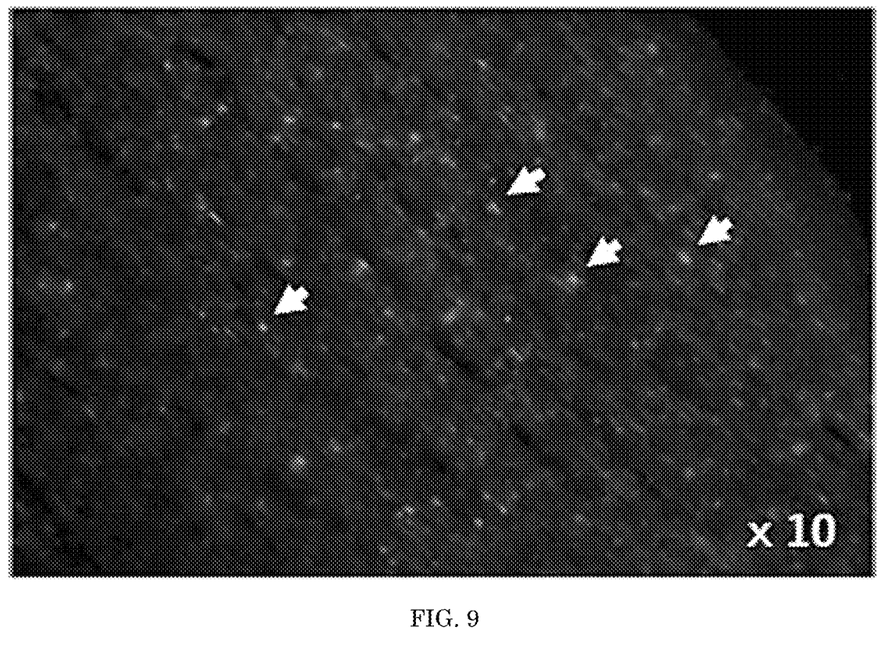
FIG. 9 It is a fluorescence micrograph (magnification×10) of a stained image by a calcium indicator (Fluo-8) of rat cerebral cortex neurons cultured on an aligned polystyrene fiber sheet. Examples of the position where the changes in fluorescence intensity due to a change in the calcium ion concentration is observed as a blinking are indicated by the arrows in the figure.

Rat cerebral cortex neurons (Thermo Fisher Scientific K. K., product number A10840), which are primary cultured neurons, were seeded on the oriented polystyrene fiber sheet as a cell scaffold at a cell density of $1.0\times10^5$ cells/cm$^2$, $3.0\times10^5$ cells/cm$^2$, or $9.0\times10^5$ cells/cm$^2$. The cells were cultured in Neurobasal (registered trademark) Medium (GIBCO, catalog number 21103-049) containing B-27 (registered trademark) Supplement (×50)/serum-free (GIBCO, catalog number 17504-044) in an incubator at 5% $CO_2$ and 37° C. for 4 weeks. The obtained cell sheet (nerve cell device) was transferred into medium containing 5 μM Fluo-8-AM (ATT Bioquest, catalog number 21081), a calcium indicator reagent, and cultured for 1 hour in an incubator at 5% $CO_2$ and 37° C. The Fluo-8-AM dye-incorporated cell sheet was set to a heat insulating plate attached to a fluorescence microscope (Olympus IX73), and fluorescence of Fluo-8-AM were observed. The change in fluorescence intensity due to a change in the calcium ion concentration is observed as a synchronized blinking (a blinking cycle of about 1.83 seconds) among the individual neurons. FIG. 9 shows the observed image by a fluorescence microscope (magnification×10). It is shown that a change in intracellular calcium concentration of neurons can be visualized (imaged) in the nerve cell device of the present invention.

The invention claimed is:

1. A nerve cell device comprising
a cell scaffold and neurons,
wherein the cell scaffold is a fiber sheet formed of a polymeric material, wherein the fiber sheet has an oriented structure in which fibers constituting the fiber sheet are aligned in one direction and when the angle in one direction is set to 0°, 80% or more of fibers are present in a range of ±30°, and
wherein a distance between fibers is 5 to 50 μm in the oriented structure, and
wherein a diameter of cross section of a fiber constituting the fiber sheet is 0.1 to 8 μm, and
wherein a thickness of the fiber sheet is 1 to 40 μm, and an opening ratio of the fiber sheet is 10 to 50%, and
wherein the neurons form a three-dimensional structure on the cell scaffold and/or in the cell scaffold, and neurons are seeded at a density of $1\times10^4$ cells/cm$^2$ to $4\times10^6$ cells/cm$^2$ against the cell scaffold.

2. The nerve cell device according to claim 1, wherein the fiber sheet is coated with an extracellular matrix protein selected from polylysine, polyornithine, laminin, fibronectin, MATRIGEL® and GELTREX®.

3. The nerve cell device according to claim 1, wherein the neurons are neural cells derived from primary cultured cells or pluripotent stem cells.

4. The nerve cell device according to claim 3, wherein the neural cells derived from the primary cultured cells or pluripotent stem cells are neural cells derived from mammals.

5. The nerve cell device according to claim 1, wherein the neurons comprise glutamatergic, dopaminergic, gamma-aminobutyratergic, monoaminergic, histaminergic or cholinergic neurons.

6. The nerve cell device according to claim 1, further comprising: a frame for holding a periphery of the nerve cell device.

7. The nerve cell device according to claim 6, wherein the frame has a longitudinal length×a lateral length of 2 mm×2 mm to 15 mm×15 mm respectively; and the frame is circular or polygonal.

8. A method for evaluating neural activity, comprising contacting the neural cell device according to claim 1 with a multi-electrode array; and measuring extracellular field potential of neural cells included in the neural cell device.

9. A nerve cell device mounting dish comprising the nerve cell device according to claim 1.

10. A nerve cell device mounting plate comprising the nerve cell device according to claim 1 included in at least one well in a multi-well plate having a plurality of wells.

* * * * *